(12) United States Patent
Sioutas et al.

(10) Patent No.: US 6,829,919 B2
(45) Date of Patent: Dec. 14, 2004

(54) HIGH-QUALITY CONTINUOUS PARTICULATE MATTER MONITOR

(75) Inventors: Constantinos Sioutas, Los Angeles, CA (US); Paul A. Solomon, Henderson, NV (US)

(73) Assignee: University of Southern California, Los Angeles, CA (US)

( * ) Notice: Subject to any disclaimer, the term of this patent is extended or adjusted under 35 U.S.C. 154(b) by 356 days.

(21) Appl. No.: 09/992,544

(22) Filed: Nov. 13, 2001

(65) Prior Publication Data

US 2002/0122177 A1 Sep. 5, 2002

Related U.S. Application Data

(60) Provisional application No. 60/248,330, filed on Nov. 13, 2000.

(51) Int. Cl.[7] .............................................. G01N 15/00
(52) U.S. Cl. ..................................... 73/28.04; 73/28.05
(58) Field of Search ............................ 73/28.04–28.06, 73/28.01, 863.22, 865.5; 356/335–336, 338–343; 250/288

(56) References Cited

U.S. PATENT DOCUMENTS

| | | | | | |
|---|---|---|---|---|---|
| 3,526,828 | A | * | 9/1970 | Whitby ........................ | 324/464 |
| 5,279,970 | A | * | 1/1994 | Patashnick et al. ..... | 73/28.04 X |
| 5,880,355 | A | * | 3/1999 | Park et al. .................. | 73/28.01 |
| 5,922,976 | A | | 7/1999 | Russell et al. ............. | 73/865.5 |
| 5,932,795 | A | * | 8/1999 | Koutrakis et al. ......... | 73/28.01 |
| 6,101,886 | A | | 8/2000 | Brenizer et al. .......... | 73/863.23 |
| 6,435,043 | B1 | * | 8/2002 | Ferguson et al. ........ | 73/863.22 |
| 6,523,393 | B1 | * | 2/2003 | Linker et al. .......... | 73/28.04 X |

FOREIGN PATENT DOCUMENTS

| | | | | |
|---|---|---|---|---|
| EP | 352126 A2 | * | 1/1990 | .............. 73/863.22 |
| JP | 7-55689 | * | 3/1995 | .......... G01N/15/02 |

OTHER PUBLICATIONS

Meyer et al., "Development of a Sample Equilibration System for the TEOM Continuous PM Monitor," J. Air & Waste Manage. Assoc., vol. 50:1345–1349 (Aug. 2000).

Patashnick and Rupprecht, "Continuous PM–10 Measurements Using the Tapered element Oscillating Microbalance," J. Air & Waste Manage. Assoc., vol. 41, 1079–1083 (Aug. 1991), No. 8.

"Development and Evaluation of a Continous Coarse ($PM_{10}$–$PM_{2.5}$) Particle Monitor," C. Misra, , M. Geller, C. Sioutas, and P. Solomon, Journal of Air and Waste Management Association, vol. 51, pp. 1309–1317 (Sep. 2001).

"Development of a Reference Standard for Particulate Matter Mass in Ambient Air," H. Patashnick, G. Rupprecht, J. L. Ambs, and M. B. Meyer, Aerosol Science and Technology, vol. 34, pp. 42–45 (2001).

"Development of Small–Cutpoint Virtual Impactors and Applications in Environmental Health, " C. Sioutas and P. Koutrakis, pp. 453–470 of Advances in Aerosol Filtration (K. Spurny, ed.) (1998) month not given.

(List continued on next page.)

Primary Examiner—Thomas P. Noland
(74) Attorney, Agent, or Firm—Fish & Richardson P.C.

(57) ABSTRACT

A system for monitoring an aerosol including a plurality of particles is provided. Each of the particles has a size. The system includes an impactor assembly to receive the aerosol at a first flow rate and remove an exhaust portion of the particles that are less than a minimum particle size or greater than a maximum particle size. A remaining portion of the particles is emitted at a second flow rate lower than the first flow rate. A first sensor measures a characteristic of the remaining portion of the particles.

21 Claims, 3 Drawing Sheets

OTHER PUBLICATIONS

"Evaluation of the TEOM Method for Measurement of Ambient Particulate Mass in Urban Areas, " G. Allen, C. Sioutas, P. Koutrakis, R. Reiss, F. W. Lurmarm, and P. T. Roberts, Air & Waste Management Assoc., vol. 47, pp. 682–689 (1997) Jun.

"Versatile Aerosol Concentration Enrichment System (VACES) for Simultaneous in vivo and in vitro Evaluation of Toxic Effects of Ultrafine, Fine and Coarse Ambient Particles Part I: Development and Laboratory Characterization, " S. Kim, P. A. Jaques, M. Chang, J. R. Froines, and C. Sioutas, Aerosol Science, vol. 32, pp. 1281–1297 (2001) month not given.

* cited by examiner

```
┌─────────────────────────┐
│  RECEIVING AN AEROSOL   │─── 70
│  AT AN INLET FLOW RATE  │
└───────────┬─────────────┘
            ▼
┌─────────────────────────┐
│   REMOVING A FIRST      │─── 72
│   RANGE OF PARTICLE     │
│        SIZES            │
└───────────┬─────────────┘
            ▼
┌─────────────────────────┐
│   REMOVING A SECOND     │─── 74
│   RANGE OF PARTICLE     │
│        SIZES            │
└───────────┬─────────────┘
            ▼
┌─────────────────────────┐
│  EMITTING THE REMAINING │─── 76
│     PORTION OF THE      │
│  AEROSOL AT AN OUTLET   │
│       FLOW RATE         │
└───────────┬─────────────┘
            ▼
┌─────────────────────────┐
│       MEASURING A       │─── 78
│  CHARACTERISTIC OF THE  │
│  REMAINING FLOW OF AIR  │
└─────────────────────────┘
```

FIG. 4

HIGH-QUALITY CONTINUOUS PARTICULATE MATTER MONITOR

CROSS-REFERENCE TO RELATED APPLICATIONS

This application claims the benefit of the filing date of U.S. provisional application No. 60/248,330 filed Nov. 13, 2000, which is hereby incorporated by reference in its entirety.

TECHNICAL FIELD

This invention relates to particulate matter monitors, and more particularly to monitors for continuous monitoring of particulate matter.

BACKGROUND

Ambient particles in the size range 2.5 to 10 $\mu$m are referred to as coarse particles or coarse mode (CM) aerosols. Coarse particles may include several potentially toxic components, such as resuspended particulate matter from paved and unpaved roads, industrial materials, brake linings, tire residues, trace metals, and bio-aerosols such as anthrax. Since a considerable fraction of these particles may deposit in the upper airways and to a lesser extent into the lower airways, they may exacerbate health conditions such as asthma or possibly cause health problems as in the case of bio-aerosols. Recent data from a small number of epidemiological studies indicate that, apart from or in addition to the fine fraction (FM) of particulate matter (also called $PM_{2.5}$), health effects also may be closely associated with the CM fraction and sometimes even to a larger extent than FM. In vitro studies with human monocytes suggest that cellular toxicity and inflammation also may be associated with the CM and its biological components.

Current measurements of both the $PM_{10}$(particulate matter having an aerodynamic diameter that is less than 10 um) and $PM_{2.5}$(particulate matter having an aerodynamic diameter that is less than 2.5 um) mass concentrations are generally based on gravimetric analysis of particles collected on filters over a period of 24 hours. Gravimetric analysis is generally used because most of the particle data used for the epidemiological studies investigating associations between mortality and morbidity outcomes and ambient particle exposures are based on PM concentrations. Typically, a time-integrated sample (e.g., over 24 hours) is collected on the filter, which is later equilibrated at designated temperature and RH conditions, and subsequently weighed to determine the mass of the deposited PM. Dividing by the amount of air sample yields the atmospheric concentration. Since the values of atmospheric parameters influencing ambient particle concentration, hence human exposure, such as the emission strengths of particle sources, temperature, RH, wind direction and speed and, mixing height, fluctuate in time scales that are substantially shorter than 24 hours, a 24-hour measurement may not reflect an accurate representation of human exposure. Thus, more accurate, better quality data on the physical-chemical characteristics of particles are needed to understand their atmospheric properties and health effects.

Techniques that are capable of providing continuous or near continuous measurements (i.e. 1-hour average or less) are highly desirable because they can provide accurate information on human exposure and atmospheric processes in short timer intervals. Over the past decade, several methods have been developed for continuous $PM_{10}$and $PM_{2.5}$mass concentration measurements. These include the Tapered Element Oscillating Microbalance (TEOM™), and a host of nephelometers such as the DataRAM™ and the DUSTTRACT™. Another nephelometer, the Continuous Ambient Mass Monitor (CAMM™), only provides measurements of FM. Mass concentration measurements using photometers or nephelometers are based on light scattering, and may be dependent on particle size and chemical composition. Variations in particle size and chemical composition may introduce considerable errors in predicting the response of nephelometers such as the DataRAM.

The TEOM™ measures either $PM_{10}$or $PM_{2.5}$(but not directly CM) by recording the decrease in the oscillation frequency of a particle-collecting element due to the increase in its mass associated with the depositing particles. In its standard configuration, the TEOM™ collects particles at a flow rate of 2–4 liter per minute (lpm) on an oscillating filter heated to 50° C. The TEOM™ filter is heated to minimize inaccuracies caused by changes in RH that can affect the amount of particle-bound water associated with the collected PM. Determining CM concentrations by difference, as currently proposed by the Environmental Protection Agency (EPA) introduces significant uncertainties in cases where FM account for a large fraction of the $PM_{10}$. Moreover, since much of the semi-volatile particulate matter (which is mostly associated with FM) may be lost from the TEOM™ filter during and after collection at 50° C., there is the potential for a substantially different measurement of $PM_{10}$mass between the TEOM™ and the Federal Reference Model (FRM). This is most likely to occur in urban areas (or areas affected by urban plumes) where volatile compounds, such as ammonium nitrate and organic compounds can comprise a substantial fraction of the FM. Heating is not likely to affect the mostly non-volatile constituents of coarse particles, thus the accuracy of CM concentrations determined as the difference between $PM_{10}$and $PM_{2.5}$may be compromised by the generally random loss of volatile compounds from FM.

In theory, continuous measurements of CM concentrations might be conducted by means of optical, electrical, and time-of-flight monitors. These monitors measure size-resolved particle concentrations based on particle numbers, which could be subsequently converted to volume concentrations assuming spherical particles and an assumption about particle density; both assumptions are required to convert particle volume to mass concentrations. As in most air sampling applications, information on particle density is generally not available and assumptions about its value will introduce uncertainties in the resulting mass concentrations estimates. A far more important limitation of the aforementioned particle number-based monitors results from the sharply decreasing number of ambient particles with increasing particle size. The ambient particle size distribution, by number, is dominated by ultrafine particles (i.e., smaller than 0.1 $\mu$m). As well, when converting a number to volume distribution, a 1.0 $\mu$m particle weighs as much as $10^3$ times a 0.1 $\mu$m particle and $10^6$ times a 0.01 $\mu$m particle. Consequently, counting errors associated with this conversion, which may be substantial for large particles, due to their relatively low numbers combined with electronic noise, may lead to significant uncertainties in volume and consequently mass as a function of particle size. This was demonstrated in a recent study by Sioutas et al, which showed that the mass concentrations obtained with the Scanning Mobility Particle Sizer/Aerodynamic Particle Sizer system were higher by 70–200% than those determined with a reference gravimetric method.

SUMMARY

A system for monitoring an aeorsol including a plurality of particles is provided. Each of the particles has a size. The system includes an impactor assembly to receive the aerosol at a first flow rate and remove an exhaust portion of the particles that are less than a minimum particle size or greater than a maximum particle size. A remaining portion of the particles is emitted at a second flow rate lower than the first flow rate. A first sensor measures a characteristic of the remaining portion of the particles.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4 is a flow diagram of a process for monitoring an aerosol.

Like reference symbols in the various drawings indicate like elements.

DETAILED DESCRIPTION

Figure 1:
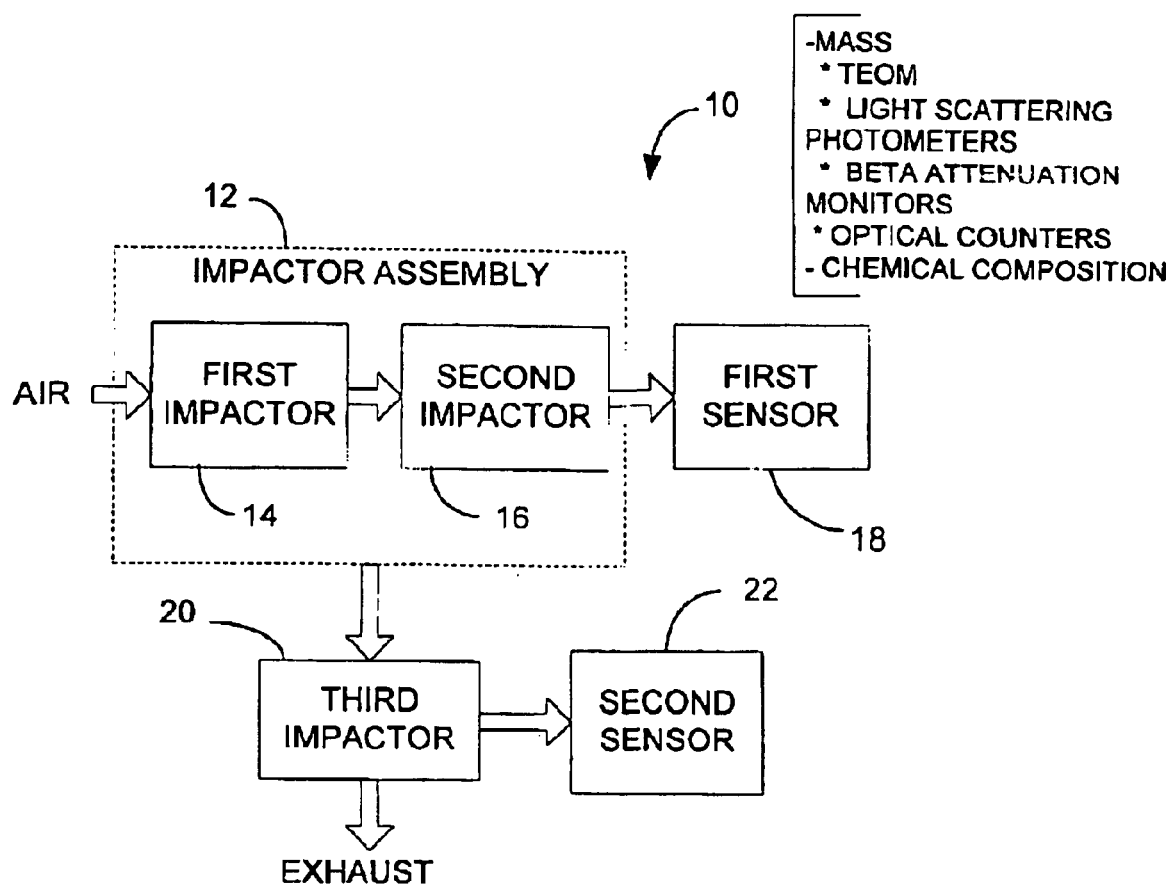
FIG. 1 is a block diagram of an embodiment of a system for monitoring an aerosol.

FIG. 1 shows an embodiment of a particulate matter monitor 10 for continuous monitoring of particulate matter. The monitor system 10 is particularly suitable for monitoring coarse particulate matter having an aerodynamic diameter of 2.5 um to 10 um. However, the monitor 10 may be used to monitor aerosols that include particulate matter having other size ranges including aerodynamic diameters between 0.25 um to 100 um. The monitor system 10 includes an impactor assembly 12 coupled to a first sensor 18. The impactor assembly 12 removes particles having an aerodynamic diameter outside of a predetermined band such as the band between 2.5 um to 10 um which is referred to as coarse particles (CP). The impactor assembly 12 includes a first impactor 14 and a second impactor 16 connected in series. Each of the impactors 14 and 16 removes a band of particles based upon the size of the particles. For example, the first impactor 14 may remove particles having an aerodynamic diameter greater than a maximum particle size, and the second impactor 16 may remove particles having an aerodynamic diameter less than a minimum particle size. The remaining portion of the particles in the aerosol predominantly have an aerodynamic diameter in the range between the minimum and maximum particle size, although there may be a minimal quantity of particles within the remaining portion that may have an aerodynamic diameter outside the range of 2.5 um to 10 um.

The impactors 14 and 16 may also concentrate the quantity of particles having a particle size between the minimum and maximum particle size so that an enriched aerosol is supplied to the first sensor 18. The particles may be concentrated by receiving an aerosol into the impactor assembly 12 at an inlet flow rate, and supplying the enriched aerosol to the first sensor 18 at an outlet flow rate that is less than the inlet flow rate. The level of concentration is a function of the ratio of the inlet flow rate to the outlet flow rate. For example, at an inlet flow rate of 50 lpm (liters per minute) and an outlet flow rate of 2 lpm, a remaining portion of particles in a band between the minimum and maximum particle size may be concentrated by a factor of about 25 while maintaining the quantity of particles that are less than the minimum particle size at about ambient concentrations.

The first sensor 18 receives the enriched aerosol from the impactor assembly 12 and continuously measures a predetermined characteristic of the particles in the aerosol. The first sensor 18 may measure particle characteristics including mass and chemical composition. Devices that may be used for measuring mass include tapered element oscillating microbalances (TEOMs), light scattering photometers, beta attenuation monitors, and optical counters. For measuring chemical composition, devices include ion chromatographs for sulfate, nitrate, sodium, and ammonium; inductively-coupled plasma mass spectrometers and graphite furnaces for trace elements and metals; thermal desporption units for organic concentrations; and mass spectrometers for detection of biologically active compounds in airborne coarse particles.

A third impactor 20 may be coupled to the impactor assembly 12 to extract another band of particle sizes to be measured by another sensor 22. The third impactor 20 may be arranged to receive a portion of the aerosol that includes particles having an aerodynamic diameter that is either less than the minimum particle size or greater than the maximum particle size. The third impactor 20 removes another portion of the particles based upon particle size so that the remaining portion includes particles having sizes within a another band of particle sizes such as between the minimum particle size and a smaller particle size that is less than the minimum particle size. For example, the impactor assembly 12 may remove particles having sizes outside the range of 2.5 um to 10 um. The third impactor 20 may then receive the exhaust aerosol from the impactor assembly 12 including particles having sizes that are less than 2.5 um. The third impactor 20 may remove particles from the exhaust aerosol having particle sizes that are less than 1.5 um. A remaining portion of the aerosol having particles with sizes in the range of 1.5 um to 2.5 um is sent to the second sensor 22 to be measured. In addition, the third impactor 20 may concentrate the particles having the selected range of sizes by emitting the aerosol at an outlet flow rate that is less than the flow rate into the third impactor 20. Further fractionate portions of the particles may be obtained by coupling further impactors and sensors to the third impactor 20 or to the impactor assembly 12.

Figure 2:
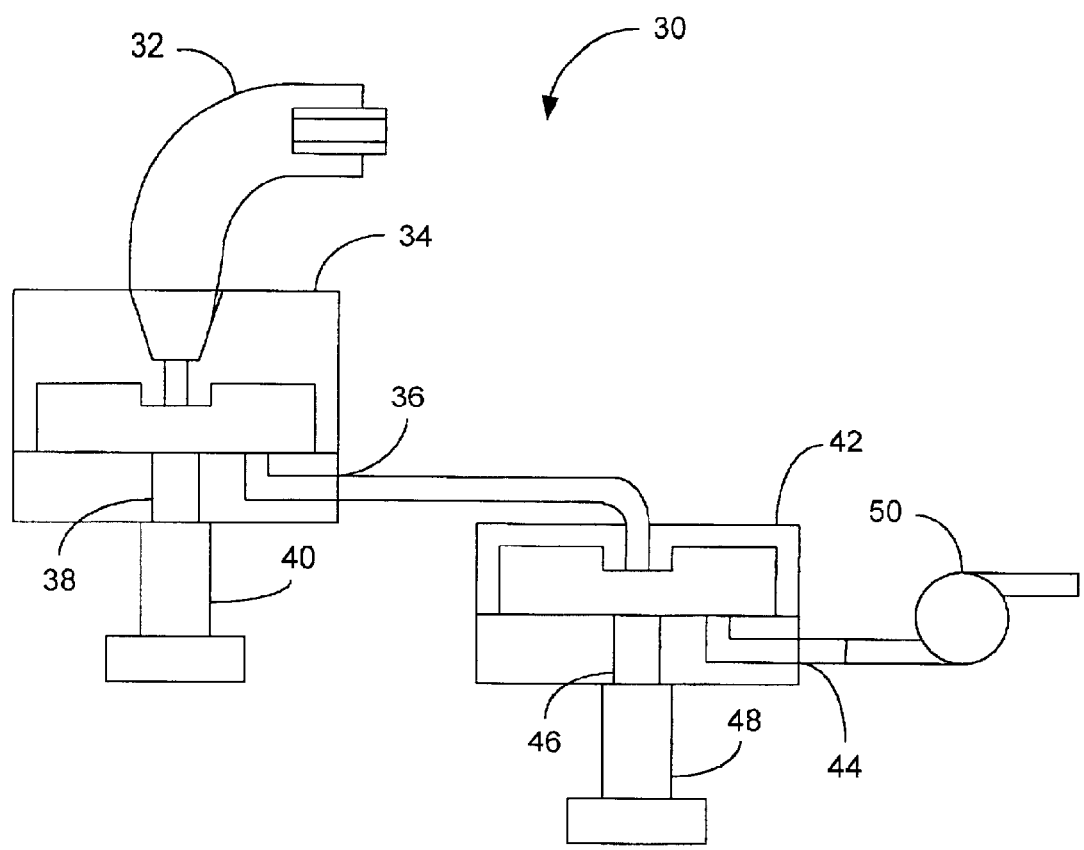
FIG. 2 is a two-dimensional diagram of a system for monitoring an aerosol.

FIG. 2 shows a two-dimensional view of an embodiment of a particulate matter (PM) monitor 30 for measuring a characteristic of PM. The PM is suspended in an aerosol that is drawn into a PM inlet 32 at about 50 lpm. The PM inlet 32 removes matter that has an aerodynamic diameter that is greater than 10 um. A first virtual impactor 34 is coupled to the PM inlet 32 to remove particles that have an aerodynamic diameter that is less than 2.5 um. The first virtual impactor 34 has a major flow 36 with a flow rate of 48 lpm, and a minor flow 38 with a flow rate of 2lpm. The major flow 36 includes the particles that have a size that is less than 2.5 um. The minor flow 38 includes an enriched aerosol of the particles ranging in size between 2.5 um and 10 um. The concentration of the selected particles is about 25 times the ambient level. The enriched aerosol additionally includes an ambient level of particles having a size that is less than 2.5 um. The minor flow 38 is coupled to a TEOM 40 that measures the mass of the PM.

The major flow 36 is coupled to a second virtual impactor 42 that extracts a fractionate portion of particles from the first virtual impactor major flow 36. The second virtual impactor 42 includes a major flow 44 having a flow rate of 46lpm and a minor flow 46 having a flow rate of 2 lpm. The minor flow 46 includes an enriched aerosol of the particles ranging in size between and 2.0 and 2.5 um. The concentration of the selected particles is about 24 times the ambient level. The enriched aerosol additionally includes an ambient level of particles having a size that is less than 2.0 um. The minor flow 46 is coupled to a TEOM 48 that measures the mass of the PM.

The second virtual impactor major flow 44 is coupled to a pump 50 that draws the aerosol through the PM inlet 32 and the virtual impactors 34 and 42.

Figure 3:
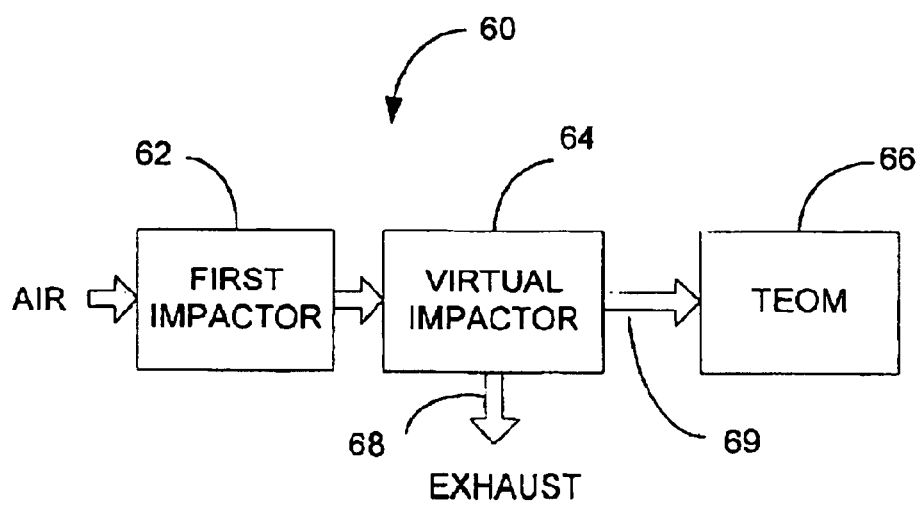
FIG. 3 is a block diagram of an embodiment of a system for monitoring an aerosol.

FIG. 3 shows another embodiment of a PM monitor 60 for measuring a characteristic of PM. The configuration of the PM monitor 60 is similar to PM monitor 30 except that the aerosol is drawn into a inlet impactor 62 before flowing through a virtual impactor 64 and into a sensor 66. The aerosol is drawn into the inlet impactor 62 at an inlet flow rate. A major flow 68 of the virtual impactor 64 exhausts particles that are smaller than a minimum particle size. A minor flow 69 of the virtual impactor 64 outputs an enriched aerosol at an outlet flow rate that is less than the inlet flow rate. The enriched aerosol includes particles that have an aerodynamic diameter that is greater than the minimum particle size. The particles are concentrated at a level above the ambient level by a factor approximately equal to the ratio of the inlet flow rate to the outlet flow rate of the virtual impactor 64. The inlet impactor 62 removes particles from the enriched aerosol that have a particle size that is greater than the maximum particle size. The remaining portion of the aerosol includes an enriched portion containing particles ranging in size between the minimum particle size and the maximum particle size, as well as an ambient level of particles that are less than the minimum particle size.

FIG. 4 shows a flow chart for a PM measurement process. Starting at block 70, an aerosol including PM is drawn into an impactor inlet at an inlet flow rate. Continuing at block 72, a first portion of particles having particle sizes in a first range is removed from the aerosol. At block 74, another portion of particles having particle sizes in a second range is also removed from the aerosol so that the remaining portion has particles that have particle sizes between a minimum particle size and a maximum particle size. Continuing to block 76, the remaining portion of the aerosol is emitted at an outlet flow rate that is less than the inlet flow rate so that the particles between the minimum particle size and the maximum particle size are concentrated in the remaining aerosol. Finishing at block 78, measuring a characteristic of the remaining aerosol.

A number of embodiments of the invention have been described. Nevertheless, it will be understood that various modifications may be made without departing from the spirit and scope of the invention. Accordingly, other embodiments are within the scope of the following claims.

What is claimed is:

1. A system for monitoring an aerosol including a plurality of particles, each of the particles having a size, comprising:

an impactor assembly to receive the aerosol at a first flow rate and remove a first portion of the particles that are less than a minimum particle size greater than a maximum particle size, a remaining portion of the particles being emitted at a second flow rate lower than the first flow rate;

at least a first sensor to measure a characteristic of the remaining portion of the particles;

an impactor to receive the first portion of the particles, the impactor to remove another portion of the received particles to leave a fractionate portion of the particles; and a second sensor to measure a characteristic of the fractionate portion of the particles.

2. The system of claim 1 wherein the characteristic of the remaining portion of the particles is selected from the group consisting of mass and chemical composition.

3. The system of claim 1 wherein the characteristic of the fractionate portion of the particles is selected from the group consisting of mass and chemical composition.

4. The system of claim 1 wherein the impactor assembly comprises:

a first impactor to remove the particles greater than the maximum particle size; and a second impactor including a first virtual impactor to remove the particles less than the minimum particle size, a first flow of the first virtual impactor to emit the remaining portion of the particles.

5. The system of claim 1 wherein the impactor assembly comprises:

a first impactor to remove the particles less than the minimum particle size; and a second impactor including a virtual impactor to remove the particles greater than the maximum particle size, a first flow of the virtual impactor to emit the remaining portion of the particles.

6. The system of claim 1 wherein the minimum particle size is about 2.5 $\mu$m and the maximum particle size is about 10 $\mu$m.

7. The system of claim 1 wherein the sensor includes a tapered element oscillating microbalance (TEOM).

8. The system of claim 1 wherein the sensor is selected from the group consisting of a TEOM, light scattering photometers, a beta attenuation monitors, optical counters, ion chromatographs, inductively-coupled plasma mass spectrometers, graphite furnaces, thermal desorption units, and mass spectrometers.

9. The system of claim 1 further comprising a pump to pull the aerosol into the impactor assembly.

10. The system of claim 9 wherein a ratio of the first flow rate to the second flow rate includes a range from 2 to 50.

11. A system for measuring a characteristic of an aerosol including a plurality of particles, each of the particles having a size, a mass, and a chemical composition, comprising:

a first impactor assembly to receive the aerosol at a first flow rate and to remove an upper range of the particles as a first function of particle size, a second impactor assembly coupled to an outlet of the first impactor to remove a lower range of the particles as a second function of particle size, a remaining portion of the particles being emitted from the second impactor assembly at a second flow rate lower than the first flow rate; and at least a first sensor to directly measure a mass of the remaining portion of the particles.

12. The system of claim 11 wherein the first sensor is also to measure a chemical composition of the remaining portion of the particles.

13. The system of claim 11 wherein the range of the particle sizes is about 2.5 $\mu$m to 10 $\mu$m.

14. The system of claim 11 wherein the first sensor includes a tapered element oscillating microbalance (TEOM).

15. The system of claim 11 further comprising a pump to pull the aerosol into the impactor assembly.

16. The system of claim 15 wherein the first flow rate includes the range of 5 lpm to 100 lpm.

17. A system comprising:
   an impactor assembly to receive the aerosol at a first flow rate, the impactor assembly including
      a first impactor subassembly to remove a first portion of the particles that are less than about 2.5 µm in size, and
      a second impactor subassembly to remove a second portion of the particles that are greater than about 10 µm in size, a remaining portion of the particles being emitted from the impactor assembly at a second flow rate lower than the first flow rate;
   a mass sensor to directly measure a mass of the remaining portion of the particles.

18. The system of claim 17, further comprising:
   an impactor to receive the first portion of the particles, the impactor to remove another portion of the particles to leave a fractionate portion of the particles; and
   a second sensor to measure a characteristic of the fractionate portion of the particles.

19. The system of claim 18, wherein the impactor comprises an impactor to remove a portion of the particles that are less than about 1.5 µm in size.

20. The system of claim 17 wherein the mass sensor comprises a microbalance.

21. The system of claim 20 wherein the mass sensor comprises a tapered element oscillating microbalance (TEOM).

* * * * *